US006620771B2

(12) United States Patent
Karol et al.

(10) Patent No.: US 6,620,771 B2
(45) Date of Patent: Sep. 16, 2003

(54) THIADIAZOLE DIMER ADDITIVES AND LUBRICATING COMPOSITIONS CONTAINING THE SAME

(75) Inventors: Thomas J. Karol, Norwalk, CT (US); Ronald J. Tepper, Fairfield, CT (US)

(73) Assignee: R. T. Vanderbilt Company, Inc., Norwalk, CT (US)

( * ) Notice: Subject to any disclaimer, the term of this patent is extended or adjusted under 35 U.S.C. 154(b) by 0 days.

(21) Appl. No.: 09/993,075

(22) Filed: Nov. 14, 2001

(65) Prior Publication Data

US 2002/0058594 A1 May 16, 2002

Related U.S. Application Data

(63) Continuation-in-part of application No. 09/693,138, filed on Oct. 20, 2000, now Pat. No. 6,365,557.
(60) Provisional application No. 60/160,568, filed on Oct. 20, 1999, and provisional application No. 60/284,982, filed on Apr. 19, 2001.

(51) Int. Cl.$^7$ .................... C10M 135/36; C07D 285/12; C07D 285/14
(52) U.S. Cl. ....................... 508/274; 548/142
(58) Field of Search ........................ 548/142; 508/274

(56) References Cited

U.S. PATENT DOCUMENTS

| | | | | |
|---|---|---|---|---|
| 3,161,575 A | * | 12/1964 | Wells et al. ............... 548/142 |
| 3,212,892 A | * | 10/1965 | von Konig et al. ......... 548/142 |
| 3,223,524 A | * | 12/1965 | von Konig .................. 548/142 |
| 4,097,387 A | * | 6/1978 | Caspari ....................... 548/142 |
| 4,136,043 A | | 1/1979 | Davis ......................... 252/47.5 |
| 4,517,103 A | | 5/1985 | Hoffman et al. ............... 252/28 |
| 4,657,942 A | * | 4/1987 | Iwasaki et al. ............. 548/142 |
| 4,795,479 A | * | 1/1989 | Karol ......................... 508/274 |
| 4,908,144 A | | 3/1990 | Davis et al. ................ 252/47.5 |
| 5,026,865 A | | 6/1991 | Karol ......................... 548/142 |
| 5,055,584 A | | 10/1991 | Karol ......................... 548/142 |
| 5,102,568 A | | 4/1992 | King et al. ................. 252/47.5 |
| 5,138,065 A | | 8/1992 | Karol ......................... 548/142 |
| 5,177,212 A | * | 1/1993 | Karol et al. ................ 548/142 |
| 5,188,746 A | | 2/1993 | Davis ......................... 252/47.5 |
| 5,194,621 A | | 3/1993 | Karol et al. ................ 548/142 |
| 5,318,712 A | | 6/1994 | Lange et al. ................ 252/47.5 |
| 5,512,190 A | | 4/1996 | Anderson ..................... 252/47 |
| 5,597,785 A | | 1/1997 | Karol ......................... 508/274 |
| 5,686,397 A | | 11/1997 | Baranski et al. ............ 508/274 |
| 5,849,925 A | | 12/1998 | Karol et al. ................ 548/142 |
| 6,150,307 A | | 11/2000 | Camenzind .................. 508/273 |
| 6,365,557 B1 | * | 4/2002 | Karol et al. ................ 508/274 |
| 6,489,484 B1 | * | 12/2002 | Karol et al. ................ 548/142 |

FOREIGN PATENT DOCUMENTS

| | | |
|---|---|---|
| EP | 0847998 | 6/1998 |
| JP | 09298107 | 5/1999 |

\* cited by examiner

*Primary Examiner*—Ellen M. McAvoy
(74) *Attorney, Agent, or Firm*—Norris McLaughlin & Marcus

(57) ABSTRACT

2,5-dimercapto-1,3,4-thiadiazole dimer-poly(ether)glycol reaction products and adducts useful as extreme pressure additives. Lubricating compositions (e.g., greases) containing reaction products and adducts exhibit improved Timken Load properties.

25 Claims, No Drawings

THIADIAZOLE DIMER ADDITIVES AND LUBRICATING COMPOSITIONS CONTAINING THE SAME

This application is a continuation-in-part of U.S. Ser. No. 09/693,138 filed Oct. 20, 2000, now U.S. Pat. No. 6,365,557; which claims the benefit of U.S. provisional application serial No. 60/160,568 filed Oct. 20, 1999. This application also claims the benefit of U.S. provisional application No. 60/284,982, filed Apr. 19, 2001.

FIELD OF THE INVENTION

The present invention relates to 2,5-dimercapto-1,3,4-thiadizaole dimer reaction products and adducts useful as extreme pressure additives, and more particularly to 2,5-dimercapto-1,3,4-thiadiazole dimer/glycol reaction products and adducts useful as extreme pressure additives.

BACKGROUND OF THE INVENTION

A variety of additives are used in lubricants to substantially improve performance. For example, extreme pressure additives are routinely incorporated into an untreated lubricating composition (e.g., greases) to significantly improve performance. Extreme pressure additives are believed to produce a film on the surface of a metal which can both increase the load carrying capacity of lubricant, and protects the metal surface under high load conditions from deterioration due to wear, welding, and abrasion.

Lead naphthenates and lead dialkyldithiocarbamates are frequently used as additives to improve the EP performance of greases. However, lead is a heavy metal which is considered "poisonous" in all forms. As an alternative, metal additives (such as antimony, zinc, and bismuth) have been used as a replacement for lead. However, these heavy metals still provide environmental concerns regarding the use. Accordingly, it has long been a goal in the art to develop non-metal lubricating materials to replace heavy metal additives while providing acceptable extreme pressure performance.

The effectiveness of potential extreme pressure additives is conventionally ascertained by the 4-Ball Weld Test (ASTM D-2596) and the Timken Load Test (ASTM D-2509). An ideal candidate compound should exhibit good results in both tests since each test quantitates different extreme pressure properties.

Known to those skilled in the art 2,5-dimercapto-1,3,4-thiadiazole (DMTD) derivatives are effective as anti-wear additives in lubricants. Examples of DMTD derivatives useful as anti-wear additives include the monosulfide and disulfide dimers of DMTD as disclosed in U.S. Pat. Nos. 4,517,103 and 5,194,621, maleate adducts of DMTD as disclosed in U.S. Pat. Nos. 5,102,568, 5,055,584 and 5,138,065 and mono-alkylated and thioacteal derivatives as disclosed in U.S. Pat. No. 5,849,925.

DMTD derivatives are also known to provide good 4-Ball Weld properties. In fact, the 4-Ball Weld properties of DMTD derivatives often exceed commercial requirements. Unfortunately, these same derivatives generally exhibit poor Timken Load performance since the DMTD derivatives do not generally provide Timken Loads levels greater than 35 pounds. As a result, commercialization of DMTD derivatives as extreme pressure additives has been limited.

In view of the above, there exists a need in the art for DMTD derivative that provide both adequate 4-Ball Weld and Timken Load properties. Accordingly, it is an object of the present invention to provide DMTD derivatives that provide adequate 4-Ball Weld and Timken Load properties, which will allow for the effective utilization of DMTD derivatives as extreme pressure additives.

SUMMARY OF THE INVENTION

The present invention provides 2,5-dimercapto-1,3,4-thiadiazole dimer/glycol reaction products and adducts useful as extreme pressure additives. In one embodiment, an additive is provided including the reaction product of:

(A) a thiadiazole dimer having formula (I):

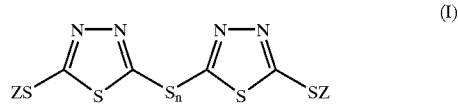

where Z is hydrogen, an alkyloxy linkage having formula (II):

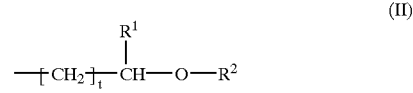

or combinations thereof, with $R^1$ being hydrogen, a branched or straight chain $C_1$ to $C_7$ alkyl radical, or combinations thereof and $R^2$ being hydrogen, a branched or straight chain $C_1$ to $C_7$ alkyl radical, or combinations thereof, with n being 1 to 2 and t being 0 or 1; and (B) a poly(ether)glycol having formula (III):

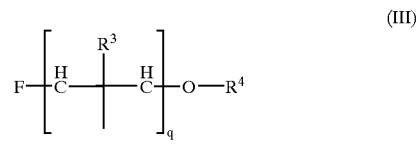

where F is a hydroxyl radical, a branched or straight chain $C_1$ to $C_{20}$ alkoxyl radical, a branched or straight chain $C_1$ to $C_{20}$ alkylcarboxyl radical, a mono-substituted, disubstituted, or tri-substituted glycerol residue, hydrogen, or combinations thereof; where $R^3$ is hydrogen, a methyl radical, or combinations thereof; where $R^4$ is hydrogen, a branched or straight chain $C_1$ to $C_{20}$ alkyl radical, a phenyl radical, a $C_1$ to $C_8$ branched or straight chain alkyl-substituted-phenyl radical, a $C_1$ to $C_{20}$ branched or straight chain acyl radical, or combinations thereof; and with q being 1 to 300.

In another embodiment, an additive is provided including monosubstituted and di-substituted thiadiazole condensation adducts having formulas (IV) and (V) respectively:

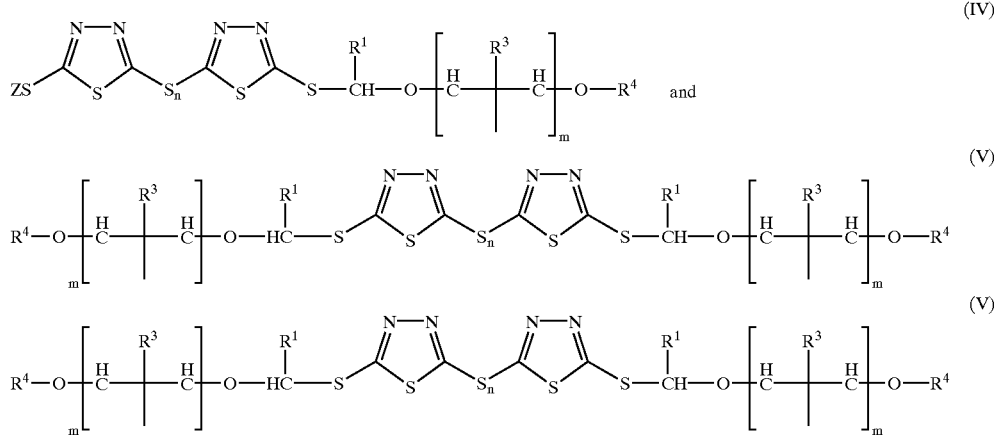

in which $R^1$, $R^3$ and $R^4$ are independently selected from the above-described group of substituents for the reaction products and n is 1 to 2. The number of repeating ether units "m" in the glycol moiety is 1 to 50.

In another embodiment, an additive is provided including the reaction product of:

(A) a thiadiazole dimer having formula (VI):

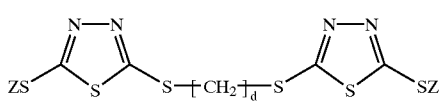

where d is 1 to 5 and Z is hydrogen, an alkyloxy linkage having formula (II):

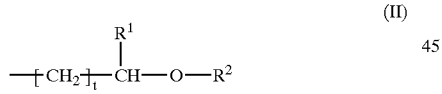

or combinations thereof, with R' being hydrogen, a branched or straight chain $C_1$ to $C_7$ alkyl radical, or combinations thereof and $R^2$ being hydrogen, a branched or straight chain $C_1$ to $C_7$ alkyl radical, or combinations thereof, wherein n is 1 to 2 and t is 0 or 1; and (B) a poly(ether)glycol having formula (III):

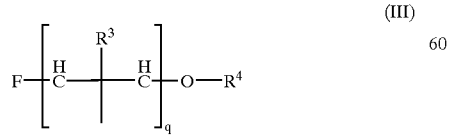

In an alternative embodiment, an additive is provided including the reaction product of:

(A) a thiadiazole compound being

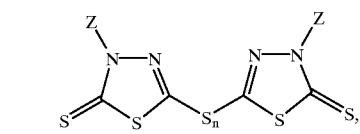

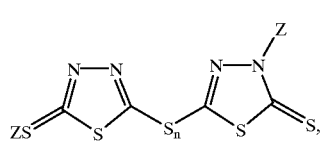

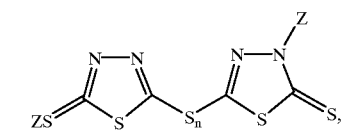

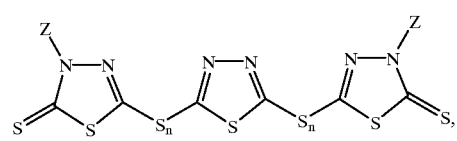

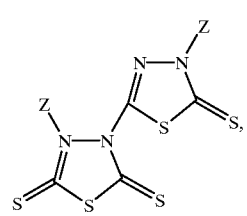

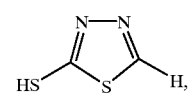

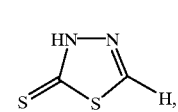

or combinations thereof, where Z is hydrogen, an alkyloxy linkage having the formula (II):

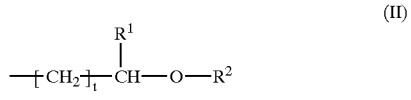

(II)

or combinations thereof, with R' being hydrogen, a branched or straight chain $C_1$ to $C_7$ alkyl radical, or combinations thereof and $R^2$ being hydrogen, a branched or straight chain $C_1$ to $C_7$ alkyl radical, or combinations thereof, where n is 1 to 2 and t is 0 or 1; and (B) a poly(ether)glycol having formula (III):

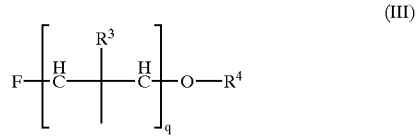

(III)

where F is a hydroxyl radical, a branched or straight chain $C_1$ to $C_{20}$ alkoxyl radical, a branched or straight chain $C_1$ to $C_{20}$ alkylcarboxyl radical, a mono-substituted, disubstituted, or tri-substituted glycerol residue, hydrogen, or combinations thereof; where $R^3$ is hydrogen, a methyl radical, or combinations thereof, where $R^4$ is hydrogen, a branched or straight chain $C_1$ to $C_{20}$ alkyl radical, a phenyl radical, a $C_1$ to $C_8$ branched or straight chain alkyl-substituted-phenyl radical, a $C_1$ to $C_{20}$ branched or straight chain acyl radical, or combinations thereof; and where q is 1 to 300.

Lubricating compositions including the reaction products and adducts of the present invention are also provided. Advantageously, the lubricating compositions of the present invention exhibit significantly improved Timken loads as compared previous DMTD derivatives. These and other advantages of the present invention will be readily apparent from the detailed description set forth below.

DETAILED DESCRIPTION OF THE INVENTION

Present invention provides reaction products and adducts of substituted-2,5-dimercapto-1,3,4-thiadiazole dimers (hereinafter "thiadiazole dimers") and poly(ether)glycols useful as extreme pressure additives in lubricants. The thiadiazole dimer-glycol reaction products and adducts have unexpectedly been found to provide good Timken Load properties in addition to good 4-Ball Weld properties. In addition, the reaction products and adducts are biodegradeble at low concentrations. Advantageously, the reaction products and adducts provide a more environmentally-friendly alternative to the heavy metal extreme pressure additives commonly used in lubricants.

In one embodiment the present invention provides an additive including a reaction product of a thiadiazole dimer and a poly(ether)glycol. The thiadiazole dimer is a 2,5-dimercapto-1,3,4-thiadiazole (DMTD) monsulfide or disulfide dimer having formula (I):

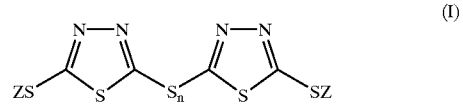

(I)

in which "n" is 1 to 2 and the substituent "Z" is either: (1) hydrogen; (2) an alkyloxy linkage having formula (II):

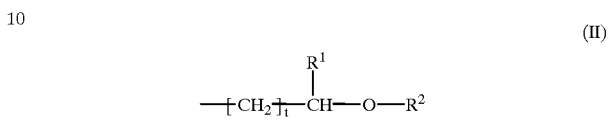

(II)

or combinations thereof. When Z is an alkyloxy linkage, "t" is 0 or 1 and the substituent $R^1$ is either: (1) hydrogen; (2) a branched or straight chain $C_1$ to $C_7$ alkyl radical, with a $C_1$ to $C_4$ alkyl radical being preferred; or a combination thereof. Likewise, the substituents for $R^2$ are independently chosen from the same group of substituents described for $R^1$. In a preferred embodiment, when Z is an alkyloxy linkage "t" is 0, $R_1$ is an ethyl radical and $R^2$ is a propyl radical.

Thiadiazole dimers falling within the above-described parameter are known in the art and are easily synthesized following known techniques. For example, the DMTD disulfide dimer (5,5'-dithiobis(1,3,4-thiadizole-2-thiol) is disclosed in U.S. Pat. Nos. 4,517,103 and 3,161,575, which are incorporated herein by reference. The DMTD disulfide dimer is also commercially available under the trade name VANLUBE® 829 from R. T. Vanderbilt, Company, Inc. The DMTD monosulfide dimer (5,5'-thiobis (1,3,4-thiadiazole-2-thiol) is also commercially under the tradename VANAX® 882A from R. T. Vanderbilt Company, Inc. The thiadiazole dimers having the alkyloxy linkage of formula (II) with "t" being zero (0) are disclosed in U.S. Pat. No. 5,194,621, which is incorporated herein by reference.

The second component for synthesizing the thiadiazole dimer-glycol reaction product is a poly(ether)glycol having formula (III):

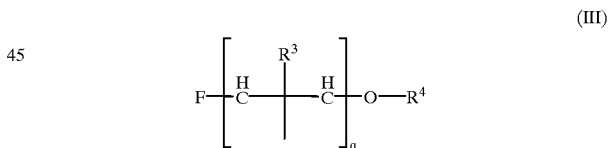

(III)

in which F is either: (1) a hydroxyl radical; (2) a branched or straight chain $C_1$ to $C_{20}$ alkoxyl radical, with a $C_1$ to $C_{10}$ radical being preferred; (3) a branched or straight chain $C_1$ to $C_{20}$ alkylcarboxyl radical, with a $C_1$ to $C_{10}$ radical being preferred; (4) a mono-substituted, di-substituted, or tri-substituted glycerol residue; (5) hydrogen; or a combination thereof. The substituent $R^3$ is either: hydrogen; a methyl radical; or a combination thereof. The substituent $R^4$ is either: (1) hydrogen; (2) a branched or straight chain $C_1$ to $C_{20}$ alkyl radical, with a $C_1$ to $C_8$ radical being preferred; (3) a phenyl radical; (4) a branched or straight chain $C_1$ to $C_{20}$ alkyl-substituted-phenyl radical, with a $C_1$ to $C_8$ alkyl substituent being preferred; (5) a branched or straight chain $C_1$ to $C_{20}$ acyl radical, with a $C_1$ to $C_{10}$ radical being preferred; or a combination thereof. The number of ether repeating units "q" ranges from 1 to 300, with 1 to 150 being preferred, with 1 to 10 being more preferred.

Poly(ether)glycols falling within the above described parameters are known in the art. Representative examples of the glycols include, but are not limited to, polyethylene glycol, polypropylene glycol, tetraethylene glycol, ethyl oxytriethylene glycol, butoxytriethylene glycol, dimethoxytriethylene glycol, triethyleneglycol di-nonanoate, butoxytriglycol, and triethyleneglycol dimethylether. One particularly preferred glycol is butoxytriethylene glycol. The glycols are commercial available from a variety of sources. Preferably, the glycols have a molecular weight from 340 to 4000, with 340 to 1000 being preferred. The glycols should have a viscosity less than 4000 centistokes at 25° C. for ease of handling. Likewise, the glycols should have a minimal effect on the dropping point of greases.

The reaction product is formed by combining the two sole components with or without a solvent and subsequently heating the components, if necessary. Preferably, the thiadiazole dimer is dispersed in the glycol, since the glycol is normally in a liquid state at room temperature. Heating the thiadiazole dimer-glycol reaction mixture is not required when the thiadiazole dimer is in a liquid state at room temperature. However, if the thiadiazole dimer is in a solid state at room temperature, the mixture may be heated (e.g., to at least 100° C.) to facilitate formation of the reaction product. The requisite temperature and time needed to facilitate formation of the reaction product is variable and can easily be determined by one skilled in the art. The formation of the liquid reaction product can approximated by observing the dissolution of the solid thiadiazole dimer. The formation of the reaction product can also be confirmed by Infrared Spectroscopy (IR) since shifts in absorption are observed when comparing the IR spectra for the individual components versus the IR spectra for the reaction product. In addition, to obtain a reaction product lighter in color, a small amount of a reducing agent (e.g., sodium meta bisulfite) is added to the reaction mixture.

The thiadiazole dimer and the poly(ether)glycol are preferably reacted in a molar ratio of the starting material of at least 0.2:1, with at least 0.4:1 being more preferred. However, for further improved extreme pressure properties an equimolar or excess of the thiadiazole starting material can be utilized (e.g., a molar ratio of 1:1, 2:1 or greater).

An alternative method for synthesizing the DMTD mono- and disulfide dimer-glycol reaction product is by reacting DMTD in the presence of the glycol. It has been found that when DMTD is dispersed in the glycol and heated the DMTD mono- and disulfide dimer forms in situ, as well as 2-mercapto-1,3,4-thiadiazole (MTD). The in situ formation of the dimer can be discerned by the contemporaneous formation of hydrogen sulfide ($H_2S$). Accordingly, one skilled in the art would react 2 moles of DMTD for 1 mole of glycol to provide a DMTD dimer-glycol reaction product having a thiadiazole:glycol starting material ratio of 1:1.

While not wishing to be limited by theory, spectroscopic analysis of the above described reaction products indicate that various isomers of the thiadiazole dimer (I) and MTD monomer may be found in the reaction mixture. The presence of these and other thiadiazole compounds is attributed to their presence in the thiadiazole starting material and to isomerization during formation of the reaction product. The thiadiazole compounds also complex with the above-described poly(ether)glycols to form reaction products useful as extreme pressure additives. Spectroscopic analysis indicates that the thiadiazole compounds have the following structures:

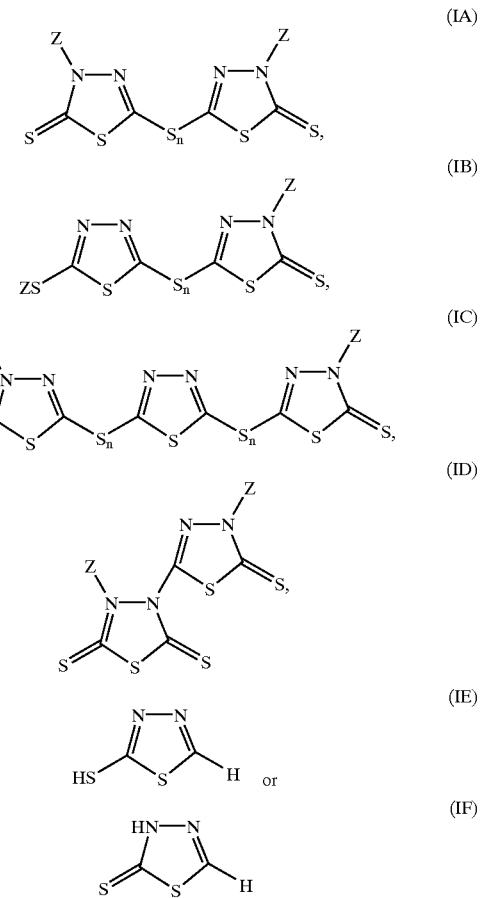

Thus, in accordance with the present invention, the additives of the present invention can further include a mixture of reaction products. In a preferred embodiment, the additive contains the reaction product of the thiadiazole dimer having formula (I) with the poly(ether)glycols as the predominate reaction product, with the remainder being any of the reaction products formed by the thiadiazole compounds of formulas (IA-IF) complexing with the poly(ether)glycols. The term "predominate" in this context preferably means at least 50 percent by weight of the total amount of the reaction products present in the additive composition. In an alternative embodiment, the present invention provides an additive that includes at least one reaction product formed from any of the thiadiazole compound having formulas (IA) through (IF) and the above-described poly(ether)glycols.

In another embodiment the present invention provides an additive including mono-substituted and di-substituted thiadiazole condensation adducts having formulas (IV) and (V) respectively:

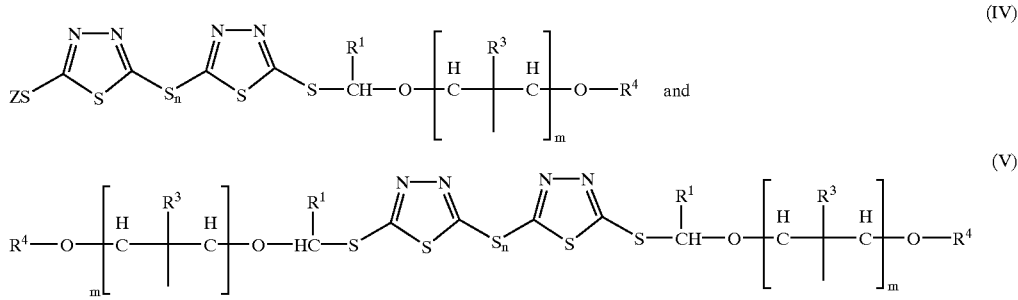

in which $R^1$, $R^3$ and $R^4$ are independently selected from the above-described group of substituents for the reaction products and n is 1 to 2. The number of repeating ether units "m" in the glycol moiety is 1 to 50, with 1 to 10 being preferred, and 1 to 3 being more preferred.

The substituted thiadiazole dimer-glycol adducts are prepared by reacting the DMTD monosulfide or disulfide dimer with an aldehyde containing the substituent $R^1$ and a poly(ether) glycol falling within the previously described parameters. The components are mixed and heated for a sufficient amount of time to form the condensation adduct. The synthesis of similar condensation adducts using monohydric alcohols instead of glycols are disclosed in U.S. Pat. No. 5,194,621, which is incorporated herein by reference. The mono-substituted thiadiazole dimer-glycol adduct is prepared by reacting the above-described components in a 1:1:1 molar ratio. The reaction mixture may also contain the di-substituted thiadiazole-glycol adduct if complete conversion of DMTD dimer does not occur. Incomplete conversion of DMTD dimer is ascertained by observing whether solid DMTD dimer remains in the reaction mixture. As will be apparent to those skilled in the art, the disubstituted thiadiazole dimer-glycol adduct is prepared by reacting the components in a 1:2:2 molar ratio. Likewise, the reaction mixture may also contain mono-substituted thiadiazole dimer adduct. These parameters can be easily modified by one skilled in the art.

In yet another embodiment, the present invention provides an additive including a thiadiazole dimer-glycol reaction product having a DMTD dimer of formula (VI):

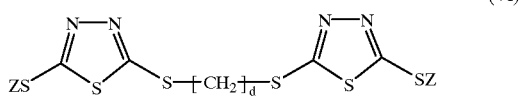

where "d" is 1 to 5, with 1 to 3 being more preferred, and Z is hydrogen, an alkyloxy linkage having formula (II) as described above, or a combination thereof. DMTD dimers having formula (VI) are easily synthesized using, techniques known in the art. The poly(ether)glycol component and ratios of DMTD dimer to poly(ether)glycol are the same as described above. A particular advantage of the DMTD dimer of formula (VI) is increased oil-solubility due to the hydrocarbon bridge.

In accordance with present invention, the thiadiazole reaction products and adducts are incorporated as additives into lubricating compositions in an effective amount to impart adequate extreme pressure properties. In this context, adequate extreme pressure properties is passing a Timken Load of at least 40 pounds, with at least 50 pounds or greater being preferred. As will be apparent with one skilled in the art, the amount of the reaction products and adducts needed to provide adequate extreme pressure properties is variable. The additives can be added in a range from 0.1 to 10 weight percent of the lubricating composition, with at least 1 weight percent being preferred and 2 weight percent being even more preferred.

Lubricating compositions suitable for incorporation of the extreme pressure additives include, but are not limited to, lubricating oils, engine oils and lubricating greases containing a major amount of base oil. A "major amount" in this context means that greater than 50 weight percent (wt. %) of the composition is base oil. Base oils to be used include, but are not limited to, napthenic, aromatic, paraffinic, mineral, and synthetic oils. Representative synthetic oils include, but are not limited to, polysiloxanes, carboxylic acid esters and polyglycol ethers.

In a preferred embodiment, the lubricating composition is a grease which is prepared by adding to a base oil thickeners such as salts and complexes of fatty acid soaps, polyurea compounds, mixed and complex soaps of alkali metals, alkaline earth metals, aluminum, modified clays and quaternary ammonium bentonite complexes. Various other additives can be incorporated as desired.

The following non-limiting examples illustrate the synthesis of the thiadiazole dimer-glycol reaction products and adducts, and their use as extreme pressure additives in lubricating compositions.

EXAMPLE 1

A thiadiazole dimer-glycol reaction product was synthesized by adding to a three-neck flask 112.9 grams of a DMTD disulfide dimer (5,5'-dithiobis(1,3,4-thiadiazole-2-thiol) (i.e., formula (I) where Z, is hydrogen ("H") and n is 2) and 138.6 grams of butoxytriethylene glycol to provide a 0.53:1 molar ratio of the starting material. The DMTD disulfide dimer is commercially available under the tradename VANLUBE® 829 from R. T. Vanderbilt, Company, Inc. The mixture, which did not contain any other reactants, was heated from 135° C. for 1 hour. After the mixture cooled, the unreacted solid material (i.e., the DMTD disulfide dimer) was removed from the liquid reaction product by filtration. The structure characteristics of this liquid reaction product (compound 1) is listed in Table 1.

EXAMPLES 2–4

Following the general procedure described in Example 1, thiadiazole dimer-glycol reaction products were prepared by mixing in a specified molar ratios the DMTD disulfide-dimer of Example 1 with poly(ether)glycols having the structure of formula (III). The substituent "Z" was either hydrogen or an alkyloxy linkage having the structure of formula (II) As in Example 1, the reaction mixtures were heated to at least 100° C. for at least 0 minutes. Once the mixtures cooled, the liquid reaction products were filtered to remove any unreacted thiadiazole dimer starting material. The structural characteristics of the reaction products (compounds 2–4) are listed in Table 1 below.

EXAMPLE 5

A thiadiazole dimer-glycol reaction product was synthesized using DMTD instead of a DMTD dimer. Approximately 16.3 grams of DMTD, 21.2 grams of triethylene glycol, and 0.14 grams of aluminum trichloride were added to a round bottom flask. The flask was attached to a scrubber containing sodium hydroxide to remove hydrogen sulfide during in situ dimer formation. The mixture was heated from 115–145° C. for 6 hours, in which $H_2S$ was observed to evolve indicating the in situ formation of the DMTD dimer. Once the reaction mixture was allowed to cool, the unreacted material was removed by filtering. The structural characteristics of the reaction product (compound 5) are listed in Table 1.

EXAMPLES 6–8

Thiadiazole dimer-glycol reaction products were prepared following the general procedure of Example 1 by mixing in specified mole ratios of thiadiazole dimer having the structure of formula (1) with poly(ether)glycols having the structure of formula (III). The substituent "Z" was either hydrogen or an alkyloxy linkage having the structure of formula II. As in Example 1, the mixtures were heated to at least 100° C. for at least 30 minutes. Once the mixtures cooled, the mixtures were filtered to remove any unreacted thiadiazole dimer starting material. The structural characteristics of the reaction products (compounds 6–8) are listed in Table I.

EXAMPLE 9

A thiadiazole dimer-glycol reaction product was synthesized by converting DMTD in situ to DMTD dimer. Approximately 267.1 grams of DMTD and 367.2 grams of butoxytriethylene glycol were added to a three-neck flask. The flask was attached to a scrubber containing sodium hydroxide to remove hydrogen sulfide during in situ dimer formation. The mixture was bubbled with nitrogen and heated to 120° C. for approximately 5½ hours. After which, the flask was attached to an aspirator and heated for an additional hour. The reaction product was then filtered. The structural characteristics of the reaction product (compound 9) are listed in Table 1. Infrared analysis of the reaction product and its components was also performed with the following major peaks being identified:

| | |
|---|---|
| DMTD bis-dimer | 1501, 1474, 1448, 1384, 1270, 1233, 1113, 1052 (cm$^{-1}$) |
| Butoxytriethylene glycol | 1460, 1351, 1297, 1248 (cm$^{-1}$) |
| Compound 9 | 1510, 1433, 1350, 1244 (cm$^{-1}$) |

COMPARATIVE EXAMPLES 10–13

Comparative thiadiazole dimer-glycol reaction products were prepared following the general procedure of Examples 6–8. The structural characteristic of the reaction products (compounds 10–13) are listed in Table 1.

TABLE 1

| Reaction Product | Z Type | n | Carbon Atoms | F | $R^3$ | q | $R^4$ | Thiadiazole: Glycol Ratio |
|---|---|---|---|---|---|---|---|---|
| Compound 1 | H | 2 | 0 | OH | H | 3 | Butyl | 0.53 |
| Compound 2 | H | 2 | 0 | OH | $CH_3$ | *(1) | OH | 5.2 |
| Compound 3 | H | 2 | 0 | OH | H | *(2) | OH | 1.0 |
| Compound 4 | H | 2 | 0 | OH | H | 4 | Butyl | 0.51 |
| Compound 5 | H | 1–2 | 0 | OH | H | 3 | OH | 0.37 |
| Compound 6 | H | 2 | 0 | OH | H, $CH_3$ | *(3) | OH | — |
| Compound 7 | H | 1 | 0 | OH | H | 3 | Butyl | 0.49 |
| Compound 8 | (II), t = 0 | 2 | 3 in $R^2$, 2 in $R^1$ | OH | H | 1 | Butyl | 1.0 |
| Compound 9 | H | 1–2 | 0 | OH | H | 3 | Butyl | 0.49 |
| Compound 10 | (II), t = 0 | 2 | 8 in $R^2$, 7 in $R^1$ | OH | H | 1 | Butyl | 1.0 |
| Compound 11 | $CH_3$ | 2 | 0 | $CH_3$ | H | 3 | $CH_3$ | 0.41 |
| Compound 12 | (II), t = 0 | 2 | 8 in $R^2$, 7 in $R^1$ | OH | N/A | 0 | Butyl | 1.0 |
| Compound 13 | (II), t = 0 | 1 | 8 in $R^1$, $R^1$ = H | OH | H | 1 | Butyl | 1.0 |

(1)Commercially available polypropylene glycol sold under the trade name JEFFOX ® PPG2000 (m.w. ≈ 2000).
(2)Commercially available polyethylene glycol sold under the trade name CARBOWAX ® 400 (m.w. ≈ 380–400).
(3)Commercially available poly(propy-,ethy-)lene glycol sold under the trade name ALKATERGE ®T-IV (m.w. - unknown).

EXAMPLE 14

A thiadiazole dimer-glycol adduct was synthesized by adding to a three-neck flask 135.9 grams of DMTD monosulfide dimer 5,5'-thiobis (1,3,4-thiadiazole-2-thiol), 16.0 grams of paraformaldehyde, and 100.1 grams of butoxytriethylene glycol to provide a 1:1:1 molar ratio of the starting material. The flask was attached to a Dean Stark apparatus and an aspirator. The mixture was heated for 1½ hours at 130° C. After the mixture cooled, the unreacted solid DMTD dimer was removed by a filtration. The structural characteristics of this liquid adduct (compound 14) is listed in Table 2. The reaction mixture is believed to contain both the mono-substituted and di-substituted DMTD dimer adducts since unreacted DMTD dimer remained in the flask.

EXAMPLES 15–19

Following the general procedure described in Example 14, thiadiazole dimer-glycol adducts were prepared by mixing either the DMTD monosulfide or disulfide dimer, with an aldehyde containing the substituent R' and a poly(ether) glycol having the structure of formula (III) in approximately a 1:1:1 molar ratio. As in Example 13, the reaction mixtures containing the three reactants were heated to at least 100° C. for at least 30 minutes. Once the reaction mixtures cooled, the adducts were filtered to remove any unreacted DMTD dimer. The structural characteristics of the liquid adducts (compounds 15–19) are listed in Table 2. As in Example 13, the reaction mixtures are believed to contain both the mono-substituted and the di-substituted DMTD dimer adducts since unreacted DMTD dimer starting material remained in the flask.

TABLE 2

| Adduct | n | $R^1$ | $R^3$ | m | $R^4$ | Substitution |
|---|---|---|---|---|---|---|
| Compound 14 | 1 | H | H | 3 | Butyl | Mono & Bis |
| Compound 15 | 2 | H | H | 3 | Butyl | Mono & Bis |
| Compound 16 | 1 | H | $CH_3$ | $35^{(1)}$ | Butyl | Mono & Bis |
| Compound 17 | 1 | H | $CH_3$ | $57^{(2)}$ | Butyl | Mono & Bis |
| Compound 18 | 1 | 3-heptyl | H | 1 | Butyl | Mono & Bis |
| Compound 19 | 1 | H | H | 1 | Butyl | Mono & Bis |

$^{(1)}$Average number for commercially available butoxypolypropylene glycol having an average molecular weight of 1550.
$^{(2)}$Average number for commercially available butoxypolypropylene glycol having an average molecular weight of 1550.

EXAMPLE 20

A di-substituted thiadiazole dimer-glycol adduct was synthesized by adding to a three-neck flask-123.0 grams of DMTD monosulfide dimer, 28.8 grams of paraformaldehyde, and 181.2 grams of butoxytriethylene glycol to provide approximately a 1:2:2 molar ratio of the starting material. As in Example 13, the flask was attached to a Dean-Stark apparatus and an aspirator. The mixture was heated from 120–135° C. for approximately 4 hours. The structural characteristics of the liquid adduct (compound 20) are listed in Table 3.

EXAMPLES 21–22

Following the general procedure of Example 20, di-substituted thiadiazole-glycol adducts were prepared by mixing DMTD monosulfide dimer, an aldehyde containing the substituent $R^1$ and a poly(ether)glycol having the structure of formula (111) in approximately a 1:2:2 molar ratio of the starting materials. As in Example 20, the mixtures were heated to at least 100° C. for at least 30 minutes. The structural characteristics of the synthesized di-substituted adducts (compounds 21–22) are listed in Table 3.

TABLE 3

| Adduct | n | $R^1$ | $R^3$ | m | $R^4$ |
|---|---|---|---|---|---|
| Compound 20 | 1 | H | H | 3 | Butyl |
| Compound 21 | 1 | H | H | 3 | Butyl |
| Compound 22 | 1 | H | H | 1 | Butyl |

EXAMPLE 23

The reaction product of Example 1 (i.e., compound 1) was evaluated for its 4-Ball Weld and Timken Load properties in accordance with ASTM D-2596, and ASTM D-2509, respectively. Grease formulations were prepared using Lithium-12 hydroxystearate grease with various weight percents (wt. %) of compound 1 as an additive. As a comparison, grease formulations containing the DMTD disulfide dimer were also evaluated. The results are listed in Table 4.

TABLE 4

| Grease Sample | Compound 1 wt. % | DMTD Dimer wt. % | 4-Ball Weld (kgf) | Timken OK Load (pounds) |
|---|---|---|---|---|
| 1 | 10% | 0 | 620 | — |
| 2 | 5% | 0 | 620 | — |
| 3 | 3% | 0 | 400 | 80 |
| 4 | 2% | 0 | 400 | 80 |
| 5 | 1% | 0 | 315 | 80 |
| 6 | 0 | 4.5% | 800 | — |
| 7 | 0 | 3.0% | 620 | — |
| 8 | 0 | 2.0% | 500 | 20 |
| 9 | 0 | 1.0% | 315 | — |

As can be seen from Table 4, sample 8 (which contained 2.0 weight percent of the DMTD disulfide dimer) exhibited a commercially acceptable 4-Ball Weld of 500 kilograms force (kgf) with a commercially unacceptable Timken OK Load of 20 pounds. To the contrary, the sample 4 (which contained 2.0 wt. % of compound 1) exhibited a commercially acceptable 4-Ball Weld Load of 500 kgf with an outstanding Timken OK Load of 80 pounds. Thus, compound 1 provided a 400% increase in Timken Load performance over the DMTD disulfide dimer.

EXAMPLE 24

Lithium-12 hydroxystearate grease formulations were prepared containing varying weight percents of DMTD disulfide dimer and butoxytriethylene glycol to ascertain the individual 4-Ball Weld and Timken Load performances of the two reactants used to synthesize compound 1. The 4-Ball Weld and Timken Load tests were conducted using the same procedure used in Example 23. The results of the 4-Ball Weld and Timken Load tests are listed in Table 5 below.

TABLE 5

| Grease Sample | DMTD Dimer wt. % | Glycol wt. % | 4-Ball Weld (kgf) | Timken OK Load (pounds) |
|---|---|---|---|---|
| 1 | 0.90 | 1.10 | 315 | 30 |
| 2 | 0.45 | 0.55 | 250 | 30 |
| 3 | 0 | 2.0 | 160 | 10 |
| 4 | 2.0 | 0 | 500 | 20 |

Table 5 shows that grease formulations containing the individual components used to synthesize compound 1 do not exhibit commercially acceptable Timken Load properties. For example, sample 1(which contained 0.90 wt. % DMTD disulfide dimer and 1.10 wt. % butoxytriethylene glycol for a total of 2.0 wt. % additive at thiadiazole:glycol molar ratio of 0.53) was only able to pass a Timken Load of 30 pounds. To the contrary, sample 4 of Table 4 (which contained 2 wt. % of compound 1—the reaction product of DMTD disulfide dimer and butoxytriethylene glycol in a 0.53 molar ratio of starting materials) was able to pass a Timken Load of 80 pounds.

EXAMPLE 25

The reaction adducts, compounds 14 and 20, were evaluated for their Timken Load properties. Grease formulations were prepared from Lithium-12 hydroxystearate grease with approximately 2 wt. % of the adduct dispersed therein. Timken Load tests were conducted following ASTM D-2509 at 80 pounds to determine the compounds efficacy. The results are listed in Table 6.

TABLE 6

| Adduct | Timken OK Load (Pass or Fail) |
|---|---|
| Compound 14 | Pass - 80 lbs. |
| Compound 20 | Pass - 80 lbs. |

EXAMPLE 26

The reaction products, inventive compound 8 and comparative compounds 10–13, were evaluated for their Timken Load properties. Grease formulations were prepared from Lithium-12 hydroxystearate grease with approximately 5 wt. % of the reaction product dispersed therein. Timken Load tests were conducted following ASTM-D-2509 at 50 pounds, and if warranted at 80 pounds, to determine efficacy. The results are listed in Table 7.

TABLE 7

| | Timken OK Load (Pass or Fail) | |
|---|---|---|
| Reaction Product | 50 lbs. | 80 lbs. |
| Compound 8 | Pass | Pass |
| Compound 10 | Fail | — |
| Compound 11 | Fail | — |
| Compound 12 | Fail | — |
| Compound 13 | Fail | — |

EXAMPLE 27

Various grease formulations were prepared containing 1 to 3 wt. % of compound 9, a DMTD mono- and disulfide dimer-butoxytriethylene glycol reaction product. Samples of the grease formulations were evaluated by the Timken Load test (ASTMD-2509), the 4-Ball Weld test (ASTMD-2596), and the 4-Ball Wear test (ASTMD-2266). The results are listed in Table 8.

TABLE 8

| Base Grease | Compound 9 (wt. %) | Timken OK Load (lbs.) | 4-Ball Weld (kgf) | 4-Ball Wear (mm) |
|---|---|---|---|---|
| Lithium-12 OH Stearate | 2.0 | 80 | 400 | 0.67 |
| | 1.5 | 70 | 315 | 0.59 |
| | 1.0 | 50 | 250 | 0.63 |
| Lithium Complex | 2.0 | 80 | 400 | 0.60 |
| | 1.5 | 60 | 315 | 0.64 |
| Aluminum Complex | 2.0 | 80 | 315 | 0.95 |
| | 1.5 | 50 | 250 | — |
| Polyurea | 3.0 | 40 | 250 | 0.84 |
| | 2.0 | 40 | 200 | 1.02 |
| Organo/Clay* | 3.0 | 60 | 250 | 0.64 |
| | 2.5 | Fail 60 | — | — |
| | 2.0 | 55 | 250 | 0.65 |

*Some softening of the grease was observed.

EXAMPLE 28

The biodegradibilty of compound 9 was evaluated following the "Proposed Standard Gledhill Shake Flask Test Method for Determining the Aerobic Aquatic Biodegradation of Lubricants and/or Their Components." This method is currently being considered by the ASTM and is known to those skilled in the art. The biodegradability assays were conducted using a commercially available apparatus. Compound 9 along with sodium benzoate (a positive control for water-soluble materials) and canola oil (a positive control for water-insoluble materials) were evaluated for 28 days using seed microorganisms sold under the trade name POLYSEED®, a product of Polybac Corporation. The biodegradability results are listed in Table 9.

TABLE 9

| Material | mg | % Degradation |
|---|---|---|
| Compound 9 | 18.2 | 78.0 |
| Compound 9 | 23.1 | 46.5 |
| Compound 9 | 52.9 | 8.4 |
| Sodium Benzoate | 36 | 78.4 |
| Canola Oil | 30.1 | 38.5 |

EXAMPLE 29

Compound 23 was prepared by converting substituent "Z" of the reaction product of Example 9 (i.e., compound 9) from hydrogen to 2-hydroxypropyl radical (i.e., formula (II) where t=1, $R_1$ is an ethyl radical and $R_2$ is hydrogen). Approximately 75 grams of the reaction product of Example 9 was placed in a three-neck flask and treated dropwise with excess propylene oxide (14.5 grams, 0.25 moles) for about two minutes. An exothermic reaction ensued and the temperature increased from 25° C. to 77° C. in about five minutes. The reaction mixture was then stirred for 15 minutes after which unreacted propylene oxide was removed by rotary evaporation.

EXAMPLE 30

Compound 24 was prepared by converting substituent "Z" of the reaction product of Example 9 (i.e., compound 9) was converted from hydrogen to a 2-hydroxybutyl radical (i.e., formula (II) where t=1, $R_1$ is a propyl radical and $R_2$ is hydrogen). Approximately 75 grams of the reaction product of Example 9 was placed in a three-neck flask and treated dropwise with excess 1,2-epoxybutane (18.0 grams, 0.25 moles) for about one minute. An exothermic reaction ensued and the temperature increased from 27° C. to 73° C. in about five minutes. The reaction mixture was then stirred for 1 hour after which unreacted 1,2-epoxybutane was removed by rotary evaporation.

EXAMPLE 31

A thiadiazole dimer-glycol reaction product (compound 25) was prepared having a DMTD dimer of formula (VI) with "d" being 2 and Z being hydrogen. The dimer was first prepared by adding to a three-neck flask 330.8 grams of a solution of the DMTD sodium half salt (33% active, 0.634 moles) and 100 mL of isopropanol. 44.0 grams of 1,2-dichloroethane (0.445 moles) was then slowly added to the mixture. An additional 133.6 grams of the DMTD half salt solution was added (for a total of 464.4 grams, 0.890 moles). The reaction mixture was heated to 80° C. and stirred for approximately three hours. The reaction mixture exhibited a significant amount of white solid precipitate. Approximately 110 mL of solvent was removed by distillation. The white solid was collected, washed with water and dried in an oven at 58° C.

The reaction product was prepared by adding 59.5 grams of the white solid and 72.7 grams of butoxytriethylene glycol to a three neck flask. The reaction mixture was heated to 128° C. for one hour after which an additional 16.7 grams of butoxytriethylene glycol was added. The mixture was heated for an additional two hours. The liquid product was filtered to remove unreacted solids. The liquid product was titrated with 0.1 M KOH, which indicated that the liquid product was 29% active. The reaction product had a thiadiazole:glycol molar ratio of approximately 0.26:1.

EXAMPLE 32

Compound 25 and its DMTD dimer component were evaluated for their Timken Load properties. Grease formulations were prepared from Lithium-12 hydroxystearate grease with approximately 5 wt. % of the additive dispersed therein. Timken Load tests were conducted following ASTM-D-2509 at 50 pounds, and if warranted at 80 pounds, to determine efficacy. The results are listed in Table 8.

TABLE 8

| Reaction Product | Timken OK Load (Pass or Fail) | |
|---|---|---|
| | 50 lbs. | 80 lbs. |
| Compound 25 | Pass | Pass |
| DMTD dimer (VI) | Fail | — |

In a further embodiment, an additive is provided included one or more of the following compositions having the formulae:

Method of Preparation:
Series A, n=1, Lot RJT-491-158:

To a three-neck flask was added 229.8 grams of 33% aqueous DMTD half salt solution (approximately 0.440 moles), 39.7 grams of 1,2-bis (2-chloroethoxy) ethane (0.212 moles) and 11 grams of water. The flask was attached to a thermometer, thermocouple, stirrer, and a condenser, and heated to approximately 95° C. for three hours. This gave an organic layer and an aqueous layer of liquid. The aqueous layer was removed, and the organic layer was washed with 200 ml of water at 70° C. The aqueous layer was again removed, and replaced with 38.9 grams of butoxytriglycol. The reaction mixture was attached to an aspirator, and heated to 112° C. to remove any remaining water. The product was then heated further to 140° C. and filtered through filter aid.

Series A, n=2, Lot RJT-491-163:

To a three-neck flask was added 60.7 grams of bis [2-(2-chloroethoxy)-ethyl] ether] (0.263 moles) and 310.4 grams of 30% DMTD half salt solution (0.541 moles). The flask was attached to a thermometer, thermocouple, stirrer Series A:

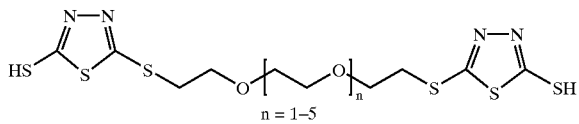

n = 1–5

Series B:

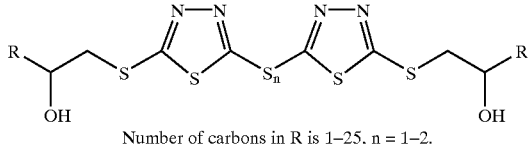

Number of carbons in R is 1–25, n = 1–2.

Series C:

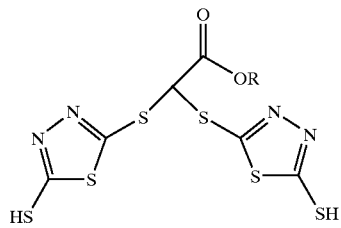

Number of carbons in R is 1–50.

Series D:

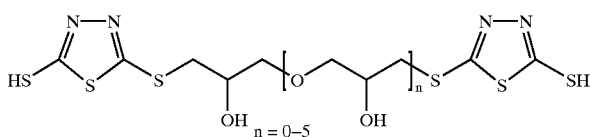

n = 0–5

Series E:

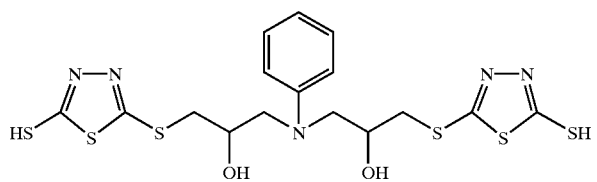

Series F:

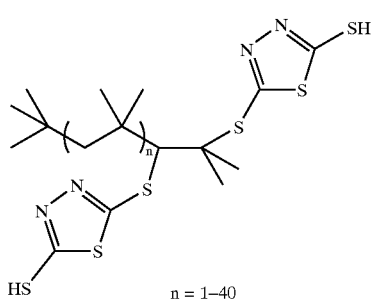

n = 1–40

Series G:

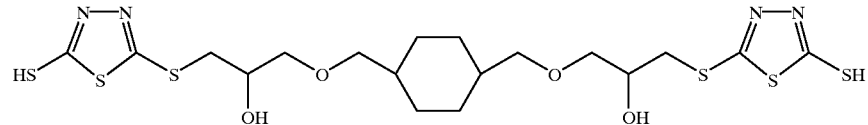

Series H:

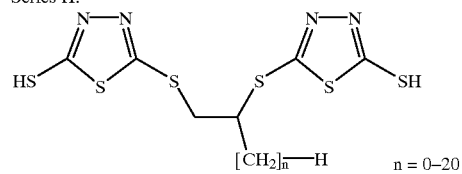

n = 0–20 and a condenser, and heated for approximately six hours at 90–100° C. Then 211 grams of DMTD salt was added and heated for one hour and the reaction was heated for one hour more at about 95° C. After cooling to room temperature, two layers of liquid were present. The upper, aqueous layer was discarded. The lower, organic layer was washed with several hundred milliliters of water, and then with several hundred milliliters of mildly acidic sulfuric acid (pH 2). The mixture was heated to 70° C. The aqueous layer was removed, washed again with water, and heated to 70° C. The water layer was again removed, and replaced with 20.6 grams of butoxytriglycol. The mixture was heated to 100° C., attached to an aspirator, and heated further to 120° C. The remaining water was removed under vacuum. The final product was then filtered through filter aid.

Preparation of Series B, Lot BT-496-9:

A sample prepared in the manner of Example 9 (75.0 g.) was treated with excess propylene oxide (14.5 g., 0.25 mole) over about two minutes. The reaction temperature increased from 25° C. to 77° C. over about five minutes. The reaction mixture was stirred for another 15 minutes and then rotary evaporated to remove any un-reacted propylene oxide leaving a dark-brown liquid.

Preparation of Series B, Lot BT-496-10:

A sample prepared in the manner of Example 9 (75.0 g.) was treated with excess 1,2-epoxybutane (18.0 g., 0.25 mole) over about one minute. The reaction temperature increased from 27° C. to 73° C. over about five minutes. The reaction mixture was stirred for another 60 minutes and then rotary evaporated to remove any un-reacted propylene oxide leaving a dark-brown liquid.

Preparation of Series C, Lot BT-496-79:

2-Ethyl-1-hexyl dichloroacetate (48.2 g., 0.200 mole) was added to a solution of aqueous monosodium DMTD (215 g. of 35.9 wt. % solution, 0.448 mole) and 2-propanol (100 g.). This mixture was heated at ca. 55° C. overnight with good agitation. After cooling, the reaction mixture was transferred to a separatory funnel. Water (ca. 100 g.) was added, the mixture gently agitated and the lower, dark-amber layer separated. This layer was rotary evaporated to remove 2-propanol and any water leaving an extremely viscous dark-amber tar. Butoxytriglycol was added to the tar and the mixture warmed with stirring giving a dark-amber liquid.

Preparation of Series C, Lot BT-496-81:

Methyl dichloroacetate (71.5 g., 0.500 mole) and aqueous monosodium DMTD (500 g. of 35.9 wt. % solution, 1.04 moles) were heated to reflux for two hours with vigorous agitation. After the mixture had cooled to about room temperature, the upper aqueous layer was poured off from the very viscous, lower, amber tar. Ethyl acetate (150 g.) and water (200 g.) were added to the tar and the mixture was warmed with agitation. The lower, organic layer was separated and rotary evaporated to remove the ethyl acetate and any water leaving a very-viscous, dark-amber tar. An equal weight of butoxytriglycol was added to the tar and the mixture was heated to about 80° C. with agitation giving a hazy, dark-amber liquid, which was suction filtered giving a clear, dark-amber liquid.

Series D, n=0, Lot BT-496-46:

A slurry of DMTD (75.1 g, 0.500 moles) in butoxytriglycol (178.3 g) was treated dropwise with epichlorohydrin (46.3 g, 0.500 moles) over a ten minute period. A cold-water bath was used to keep the reaction from exceeding 55° C. during the addition. An aqueous monosodium DMTD salt was then added (270 g of a 33% solution, approximately 0.52 moles) while stirring. The solution changed from a clear yellow solution to a slightly hazy amber colored solution, and the temperature increased from 28 to 33° C. The solution was then heated to distill off the water. Water began to distill off at 107° C. The solution was heated at 145° C. until most of the water was removed. The product was a dark amber, viscous liquid. This product was filtered at about 60–65° C. to remove the sodium chloride side product.

Series D, n=2, Lot BT-496-48:

A three-neck flask was charged with 150.2 g of DMTD (1.00 moles) and 252.3 g of butoxytriglycol. Glycerol diglycidyl ether (102.1 g, 0.50 moles) was added dropwise over a period of 30 minutes. A cold-water bath was used to keep the reaction temperature below 45° C. The product was a viscous, nearly clear greenish amber liquid. Suction filtration gave a clear liquid.

Series E, Lot BT-496-49:

A mixture of DMTD (150.2 g., 1.00 moles) and 253 g of butoxytriglycol was treated dropwise with N,N-diglycidylaniline (102.6 g, 0.500 moles). The temperature of the reaction mixture was not allowed to exceed 60° C. by using an ice water bath and by adjusting the rate of addition of the epoxide. After all the epoxide had been added, the reaction mixture was stirred at 50–60° C. for about 30 minutes. The product was a clear amber liquid that did not require filtering.

Preparation of Series F, n=1, lot RJT-491-180:

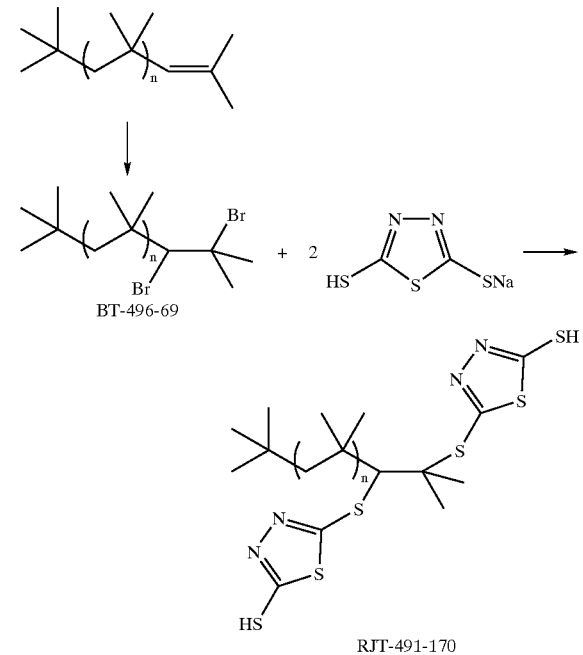

Bromination of Triisobutylene:

Triisobutylene was treated dropwise with bromine until the reddish-brown color of bromine persisted for a few minutes. HBr evolved throughout the addition. Additional Bromine was added until no more HBr was being evolved, and a dark reddish-brown color remained for several hours without fading. The material was extracted twice with water, rotary evaporated, and suction filtered to remove HBr and bromine, leaving a clear, amber liquid.

Treatment of Brominated Triisobutylene with DMTD Half Salt:

To a three neck flask was added 143.0 grams of the brominated form of triisobutylene (BT-496-69) (0.436 moles), 424.8 grams of 36% DMTD half salt solution (0.888 moles), and 84.5 grams of isopropanol. The mixture was heated to 86° C. for three hours. The mixture was then heated to 110° C. and the isopropanol was removed by distillation. Upon cooling to room temperature, this gave a viscous solid and an aqueous solution. The aqueous solution was removed, and the solid was washed with fresh water at 70° C.

Preparation of butoxytriglycol Complex of DMTD Adduct:

To a three neck flask was added 138.1 grams of the DMTD bis dimer adduct to triisobutylene (RJT-491-170) and 59.2 grams of butoxytriglycol. All of the solid dissolved when the mixture was heated to 110° C. The mixture was heated further to 125° C. and filtered through filter aid.

Series G, Lot BT-496-41:

A mixture of DMTD (30.0 g, 0.20 moles) and butoxytriglycol was treated drop-wise with 1,4-cyclohexanedimethanoldiglycidyl ether (25.6 g, 0.1 moles). The epoxide was added at such a rate that the reaction temperature did not exceed 70° C. The reaction mixture changed from a yellow slurry to a clear yellow amber solution during the addition.

Series H, n=2, Lot RJT-491-184:

To a three-neck flask was added 91.9 grams of 1,2-dibromobutane (0.426 moles), 423.0 grams of 36% DMTD half salt solution (0.884 moles), and approximately 150 ml of 2-propanol. The reaction was heated for about two and one half hours at 85° C. The reaction was then heated further, removing the 2-propanol by distillation. This gave a solid precipitate, which was transferred to a sintered glass funnel. The solid was washed further with several hundred milliliters of warm water. The product was then dried, and 127.5 grams of the material was added to a second three-neck flask with 127.6 grams of butoxytriglycol. The mixture was heated to 114° C., until all of the solid dissolved. The product was then filtered through filter aid.

Additional Possible Isomers:

The reactions of DMTD with epoxide derivatives, which are shown above, were all assumed to react at the less hindered carbon atom of the epoxide and on the sulfur atom of the DMTD. However, there may be additional isomers, which have reacted at the more hindered carbon atom of the epoxide or on one of the nitrogen atoms of the DMTD. For example, in series D, where n=0 (lot BT-496-46), this would also produce:

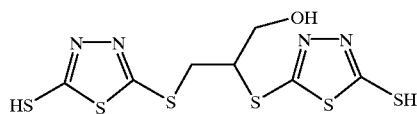

Additional possible isomers, which may also be included are shown below:

Series B:

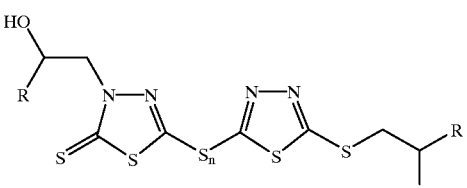

n = 1–2 and

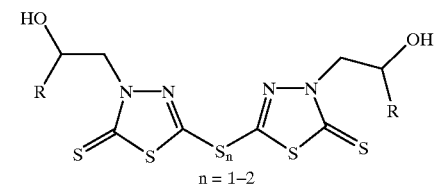

n = 1–2

Since a preparation of Example 9 was used as the reagent, it would seem likely that all forms of epoxidized thiadiazole derivatives contained in Example 9 would also be present:

These include:

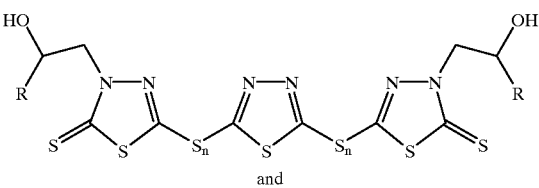

and

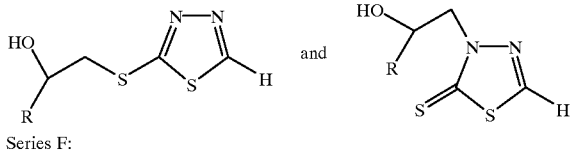

Series F:

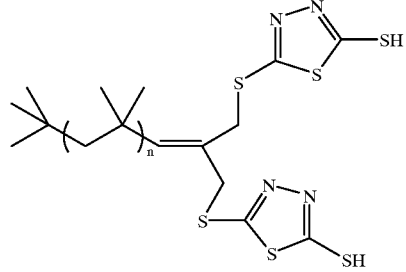

and

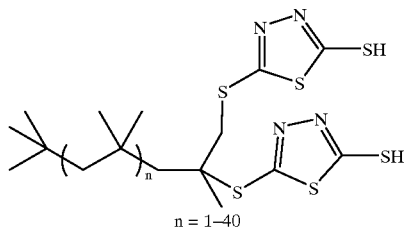

n = 1–40

Efficacy of the above compositions was demonstrated as follows:

| Series | n | R | Conc., mass % in BTG | Lot | Testing |
|---|---|---|---|---|---|
| A | 1 | — | 60 | RJT-491-158 | 80 Lb Timken, 400 kgf 4-Ball Weld Point at 2.0% in Exxon Li 12-OH Stearate Grease. 60 Lb. Timken, 250 kgf 4-ball Weld Point at 1.0% in Exxon Li 12-OH Stearate Grease. |
| A | 2 | — | 72 | RJT-491-163 | 60 Lb Timken, 315 kgf 4-Ball Weld Point at 2.0% in Exxon Li 12-OH Stearate Grease. |
| B | 1–2 | Methyl | 48 | BT-496-9 | 250 kgf 4-Ball Weld Point at 2.0% in Hatcol 2970. |
| B | 1–2 | Ethyl | 50 | BT-496-10 | 250 kgf 4-Ball Weld Point at 2.0% in Hatcol 2970. |
| C | — | 2-ethylhexyl | 60 | BT-496-79 | 250 kgf 4-Ball Weld Point, at 2.0% in Hatcol 2970. |
| C | — | methyl | 50 | BT-496-81 | 80 Lb. Timken, 315 kgf 4-Ball Weld point in Exxon Li 12-OH Stearate Grease at 2.0%. |
| D | 0 | — | 50 | BT-496-46 | 80 Lb Timken, 400 kgf 4-Ball Weld Point, 0.49 mm 4-Ball Wear Scar Diameter (mm) at 2.0% in Exxon Li 12-OH Stearate Grease. 40 Lb Timken, 400 kgf 4-Ball Weld Point, 0.56 mm 4-Ball Wear Scar Diameter (mm) at 1.5% in Exxon Li 12-OH Stearate Grease. |
| D | 2 | — | 50 | BT-496-48 | 250 4-Ball E.P. Weld Point, kgf, in Exxon Li 12-OH Stearate Grease at 2.0%. |
| E | — | — | 50 | BT-496-49 | 400 4-Ball E.P. Weld Point, kgf, in Exxon Li 12-OH Stearate Grease at 2.0%. |
| F | 1 | — | 70 | RJT-491-180 | 315 4-Ball E.P. Weld Point, kgf, in Exxon Li 12-OH Stearate Grease at 2.0%. |
| G | — | — | 50 | BT-496-41 | 315 4-Ball E.P. Weld Point, kgf, in Exxon Li 12-OH Stearate Grease at 2.0%. |
| H | 2 | — | 50 | RJT-491-184 | 315 4-Ball E.P. Weld Point, kgf, in Exxon Li 12-OH Stearate Grease at 2.0%. |

| Lot | Z Type | n | Carbon Atoms | F | $R^3$ | q | R4 | Thiadiazole: Glycol Ratio |
|---|---|---|---|---|---|---|---|---|
| RJT-491-158 | H | 1 | 0 | OH | H | 3 | Butyl | 0.746 |
| RJT-491-163 | H | 2 | 0 | OH | H | 3 | Butyl | 1.156 |
| BT-496-9 | II, t = 1 | 1–2 | 1 in R1 R2 = H | OH | H | 3 | Butyl | 0.498 |
| BT-496-10 | II, t = 1 | 1–2 | 2 in R1 R2 = H | OH | H | 3 | Butyl | 0.502 |
| BT-496-79 | H | — | 0 | OH | H | 3 | Butyl | 0.660 |
| BT-496-81 | H | — | 0 | OH | H | 3 | Butyl | 0.557 |
| BT-496-46 | H | 0 | 0 | OH | H | 3 | Butyl | 0.579 |
| BT-496-48 | H | 2 | 0 | OH | H | 3 | Butyl | 0.409 |
| BT-496-49 | H | — | 0 | OH | H | 3 | Butyl | 0.408 |
| RJT-491-180 | H | 1 | 0 | OH | H | 3 | Butyl | 1.031 |
| BT-496-41 | H | — | 0 | OH | H | 3 | Butyl | 0.370 |
| RJT-491-184 | H | 2 | 0 | OH | H | 3 | Butyl | 0.582 |

BTG = Butoxytriglycol

What is claimed is:

1. An additive for use in lubricants having the structural formula (VII):

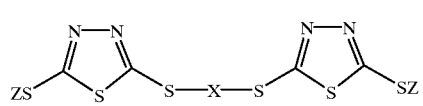
(VII)

wherein:
Z is selected from the group consisting of hydrogen, an alkoxy linkage having formula (II)

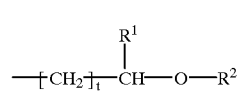
(II)

and combination thereof,
wherein:
R$^1$ and R$^2$ are selected from the group consisting of hydrogen, a branched or straight chain C$_1$–C$_7$ alkyl radical, and combinations thereof; and
t is 0 or 1; and
X is selected from the group consisting of:

(a)

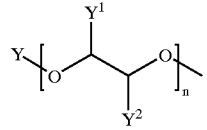

wherein:
Y is an alkylene radical optionally substituted with hydroxyl;
Y$^1$ is hydrogen;
Y$^2$ is selected from the group consisting of hydrogen and hydroxyl and n=0 to 5, wherein Y is substituted with hydroxyl when n=0 and Y$^2$ is hydroxyl when n=1; and
(b) Y—Z$^1$—Y
wherein:
Y is an alkylene radical which is optionally substituted with a hydroxyl; and
Z$^1$ is an hetero atom wherein said hetero atom is optionally substituted with an alkyl or aryl groups; and
(c) Y—Z$^1$—Y
wherein:
Y is a substituted or unsubstituted ether radical; and
Z$^1$ is a cycloalkyl, aryl or heterocyclic ring.

2. The additive of claim 1 wherein the additive has the structural formula

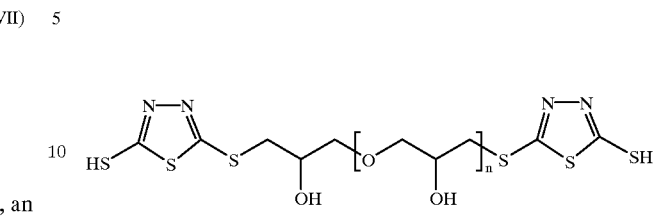

wherein n=0 to 5.

3. The additive of claim 1 wherein the additive has the structural formula

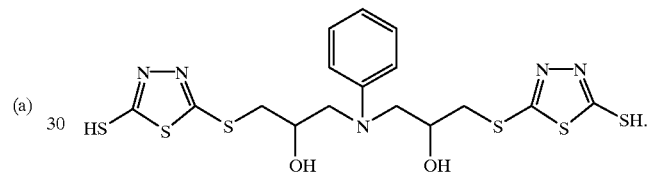

4. The additive of claim 1 wherein the additive has the structural formula

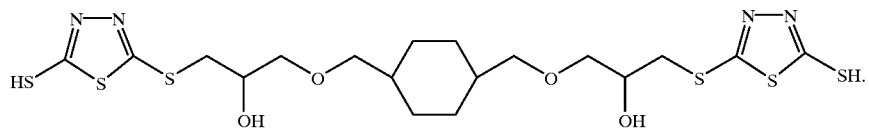

5. An additive for use in lubricants comprising of the reaction product of:

(A) a thiadiazole monomer and dimer compound having the structural formula (I) and (Ia) respectively

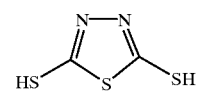
(I)

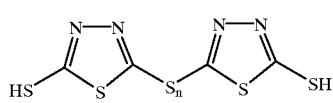
(Ia)

wherein:
n is 1 to 2; and (B) an epoxy compound having the structural formula

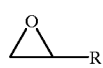

wherein:
R is a branched or straight chain $C_1$–$C_{25}$ alkane, branched or straight chain $C_1$–$C_{25}$ alkene, branched or straight chain $C_1$–$C_{25}$ alkyne, $C_3$–$C_{25}$ arene, branched or straight chain $C_1$–$C_{25}$ alkylarene, branched or straight chain $C_1$–$C_{25}$ alkenylarene, branched or straight chain $C_1$–$C_{25}$ alkynylarene, branched or straight chain $C_1$–$C_{25}$ arylalkane, branched or straight chain $C_1$–$C_{25}$ arylalkene and branched or straight chain $C_1$–$C_{25}$ arylalkyne.

6. The additive of claim 5 wherein the additive has the structural formula

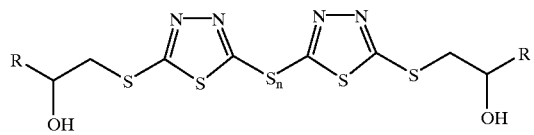

wherein n and R are as defined in claim 5.

7. The additive of claim 5 wherein the additive has the structural formula

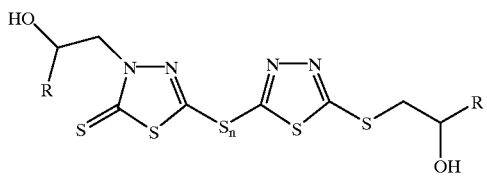

wherein n and R are as defined in claim 5.

8. The additive of claim 5 wherein the additive has the structural formula

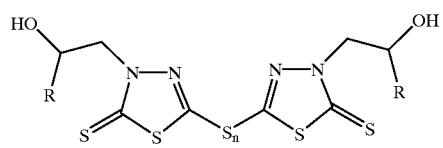

wherein n and R are as defined in claim 5.

9. The additive of claim 5 wherein the additive has the structural formula

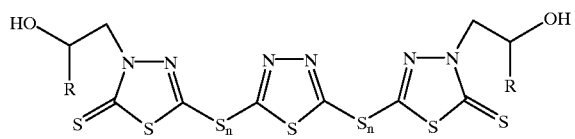

wherein n and R are as defined in claim 5.

10. The additive of claim 5 wherein the additive has the structural formula

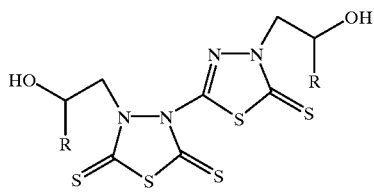

wherein n and R are as defined in claim 5.

11. The additive of claim 5 wherein the additive has the structural formula

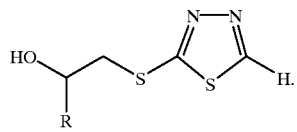

12. The additive of claim 5 wherein the additive has the structural formula

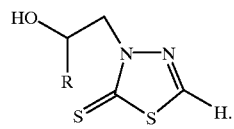

13. A lubricating composition comprising a major amount of a base oil and an effective amount of the additive of claim 5.

14. An additive for use in lubricants comprising of the reaction product of:

(VIII)

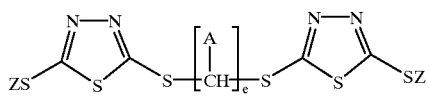

wherein:
Z is selected from the group consisting of hydrogen, an alkoxy linkage having formula (II)

(II)

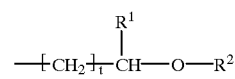

and combination thereof,
wherein:
$R^1$ and $R^2$ are selected from the group consisting of hydrogen, a branched or straight chain $C_1$–$C_7$ alkyl radical, and combinations thereof; and
t is 0 or 1;
A is hydrogen, branched or straight chain, substituted or unsubstituted alkyl, COOR or combinations thereof,
wherein:
R is a branched or straight chain $C_1$–$C_{50}$ alkane, branched or straight chain $C_1$–$C_{50}$ alkene, branched or straight chain $C_1$–$C_{50}$ alkyne, $C_3$–$C_{50}$ arene, branched or straight chain $C_1$–$C_{50}$ alkylarene, branched or straight chain $C_1$–$C_{50}$ alkenylarene, branched or straight chain $C_1$–$C_{50}$ alkynylarene, branched or straight chain $C_1$–$C_{50}$ arylalkane, branched or straight chain $C_1$–$C_{50}$ arylalkene and branched or straight chain $C_1$–$C_{50}$ arylalkyne; and e is 1 to 2;

wherein at least one A is not hydrogen when both Z are hydrogen or at least one Z is not hydrogen when A is hydrogen.

15. The additive of claim 14 wherein the additive has the structural formula

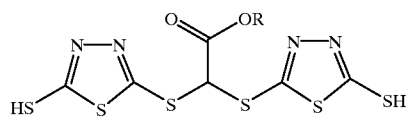

wherein R is as defined in claim 14.

16. The additive of claim 14 wherein the additive has the structural formula

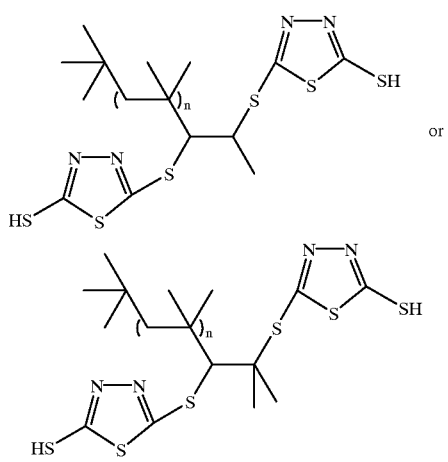

wherein n is 1 to 40.

17. The additive of claim 16 wherein n=1 to 10.

18. The additive of claim 16 wherein n=11 to 20.

19. The additive of claim 16 wherein n=21 to 30.

20. The additive of claim 16 wherein n=31 to 40.

21. The additive of claim 14 wherein the additive has the structural formula

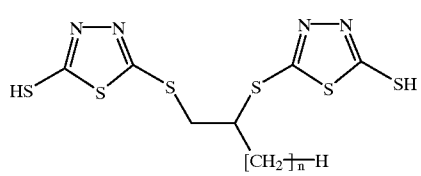

wherein in n is 1 to 20.

22. An additive for use in lubricants having the structural formula:

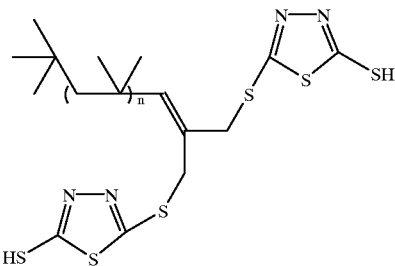

wherein n=1 to 40.

23. A lubricating composition comprising a major amount of a base oil and an effective amount of the additive of claim 22.

24. A lubricating composition comprising a major amount of a base oil and an effective amount of the additive having the structural formula (VII):

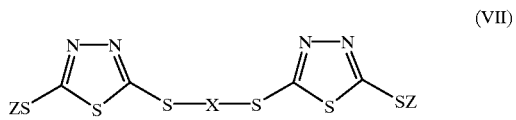

(VII)

wherein:
Z is selected from the group consisting of hydrogen, an alkoxy linkage having formula (II)

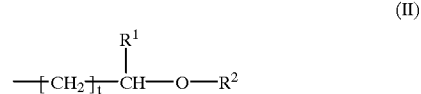

(II)

and combination thereof,
wherein:
$R^1$ and $R^2$ are selected from the group consisting of hydrogen, a branched or straight chain $C_1$–$C_7$ alkyl radical, and combinations thereof; and t is 0 or 1; and X is selected from the group consisting of:

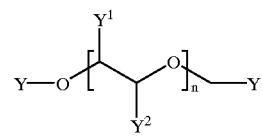

(a)

wherein:
Y is an alkylene radical;
$Y^1$ and $Y^2$ are hydrogen and n=1 to 5; and

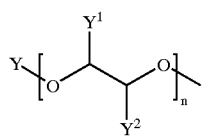

(b)

wherein:
Y is an alkylene radical optionally substituted with hydroxyl;
$Y^1$ is hydrogen,
$Y^2$ is selected from the group consisting of hydrogen and hydroxyl; and
n=0 to 5; and
(c) Y—$Z^1$—Y
wherein:
Y is an alkylene radical which is optionally substituted with a hydroxyl; and
$Z^1$ is an hetero atom wherein said hetero atom is optionally substituted with an alkyl or aryl groups; and
(d) Y—$Z^1$—Y
wherein:
Y is a substituted or unsubstituted ether radical; and
is a cycloalkyl, aryl or heterocyclic ring.

25. A lubricating composition comprising a major amount of a base oil and an effective amount of an additive for use in lubricants comprising of the reaction product of:

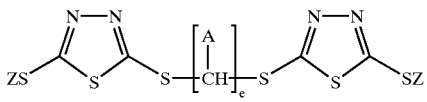

(VIII)

wherein:
Z is selected from the group consisting of hydrogen, an alkoxy linkage having formula (II) and combination thereof,
wherein:
$R^1$ and $R^2$ are selected from the group consisting of hydrogen, a branched or straight chain $C_1$–$C_7$ alkyl radical, and combinations thereof; and
t is 0 or 1;
A is branched or straight chain, substituted alkyl or COOR or combinations thereof,
wherein:
R is a branched or straight chain $C_1$–$C_{50}$ alkane, branched or straight chain $C_1$–$C_{50}$ alkene, branched or straight chain $C_1$–$C_{50}$ alkyne, $C_3$–$C_{50}$ arene, branched or straight chain $C_1$–$C_{50}$ alkylarene, branched or straight chain $C_1$–$C_{50}$ alkenylarene, branched or straight chain $C_1$–$C_{50}$ alkynylarene, branched or straight chain $C_1$–$C_{50}$ arylalkane, branched or straight chain $C_1$–$C_{50}$ arylalkene and branched or straight chain $C_1$–$C_{50}$ arylalkyne; and
e is 1 to 2.

\* \* \* \* \*